United States Patent [19]

Smith

[11] Patent Number: 4,581,772

[45] Date of Patent: Apr. 15, 1986

[54] TRAINING PANTY

[76] Inventor: Alice G. Smith, 804 S. Story Rd., Irving, Tex. 75060

[21] Appl. No.: 594,257

[22] Filed: Mar. 28, 1984

[51] Int. Cl.$^4$ ............................................. A41B 9/00
[52] U.S. Cl. ........................................................ 2/111
[58] Field of Search ........ 604/365, 366, 367, 370–372, 604/381, 385, 391, 399; 2/111, 228, 238, 402, 404, 406, 407

[56] References Cited

U.S. PATENT DOCUMENTS

| | | | |
|---|---|---|---|
| 2,726,398 | 12/1955 | Rosenberg | 2/402 |
| 2,771,881 | 11/1956 | Betts | 2/402 |
| 3,150,664 | 9/1964 | Noel | 604/391 |
| 3,618,608 | 11/1971 | Brink | . |
| 4,051,854 | 10/1977 | Aaron | . |
| 4,145,763 | 3/1979 | Abrams et al. | . |
| 4,241,462 | 12/1980 | Tagawa et al. | . |
| 4,280,230 | 7/1981 | Lafleur | . |
| 4,338,938 | 7/1982 | Seavitt | 604/386 |
| 4,402,690 | 9/1983 | Redfern | . |
| 4,410,327 | 10/1983 | Baggaley | . |

Primary Examiner—Doris L. Troutman

[57] ABSTRACT

A training panty (10) includes a pair of pants (12) having a front panel (14) and a rear panel (16) integrally joined together at a crotch (18). Releasable contact fastening members (30, 38) are positioned on opposing surfaces of front panel (14) and rear panel (16), respectively along the lateral edges thereof so that front panel (14) and rear panel (16) can be releasably secured together to define a waistband (20) and a pair of identical leg openings (22). In an alternative embodiment, front panel (14) is substantially smaller than rear panel (16) and is constructed to overlay the front midsection only of the body of the child wearer. In that embodiment, rear panel (16) is constructed to partially encircle the child's body and to be releasably secured to front panel (14) at a location proximate the front midsection of the child's body.

6 Claims, 4 Drawing Figures

TRAINING PANTY

TECHNICAL FIELD OF THE INVENTION

This invention relates generally to undergarments for very young children, and more specifically to training panties.

BACKGROUND OF THE INVENTION

Training panty type garments are well known and are commonly used for very young children during the period in which a child is being taught to control urination and other natural bodily functions. During the training period, the child is taught to remove the training panty before performing certain bodily functions and to replace the garment once the function is completed. The training panty is thus ideally constructed so that it is easily removed and replaced by the child wearer.

Because the child is not always able to exercise the requisite control over his bodily functions, it is often necessary to remove the garment to clean the child. It is important therefore that the garment be additionally constructed so that it can be easily removed to provide access to the child's body and thus facilitate cleaning of the child's buttocks. The garment must also be constructed for very secure attachment so that it is not loosened by the movement of an active child.

Previous training panties have suffered from various limitations and have not been easily removed and replaced by the child. Those panties have also presented problems of access to the child's body, and have sometimes not been able to be securely fastened about the child.

The present training panty obviates those disadvantages by providing an improved training panty that is comfortable to the child wearer and which can be easily removed and replaced by the child as necessary to perform natural bodily functions. The present training panty includes releasable contact fastening means on its front and rear panels which facilitate removal of the garment when it becomes soiled and allow for easy access to the child's body for cleaning. The releasable contact fastening means may also be selectively engaged to control the overlap of the front and rear panels to adjust the training panty to the size of the child and thus provide greater comfort.

SUMMARY OF THE INVENTION

The present invention described and disclosed herein comprises an improved training panty which is simple in construction, is comfortable for the child wearer, and which can be easily removed and replaced by the child as necessary to perform natural bodily functions. The training panty can also be easily and conveniently removed to provide access to the child's body for cleaning, while being able to be very securely attached during use.

More specifically, the training panty of the present invention comprises a pair of cloth pants having a front panel and a rear panel integrally joined together at a crotch. Releasable contact fastening means are positioned on opposing surfaces of the front and rear panels along the lateral edges thereof so that the front and rear panels are releasably secured together to define a waistband and a pair of identical leg openings. The releasable contact fastening means facilitate removal of the garment when it becomes soiled and allow for selectively opening and closing the garment to thus provide easy access to the child's body for cleaning.

BRIEF DESCRIPTION OF THE DRAWINGS

A more complete understanding of the invention can be had by reference to the following detailed description taken in conjunction with the accompanying drawings in which.

DETAILED DESCRIPTION OF THE INVENTION

Figure 1:
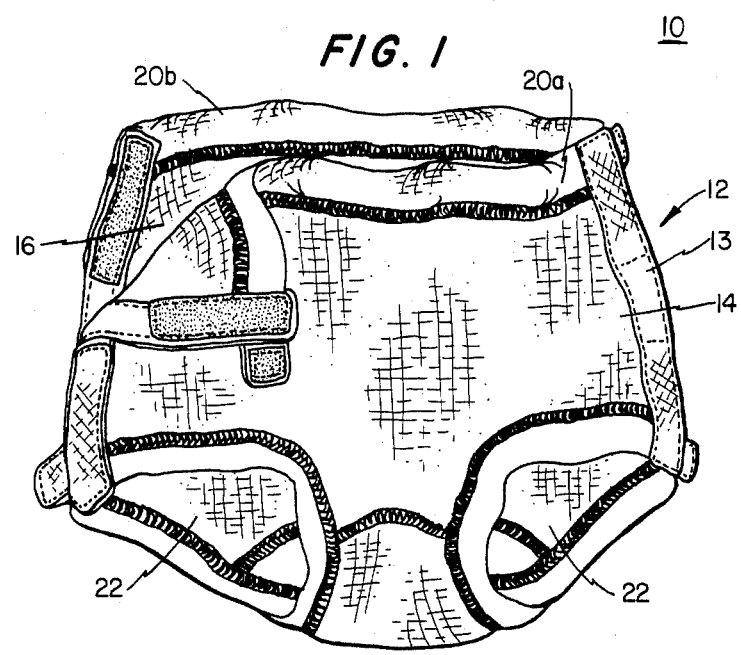
FIG. 1 is a perspective view of the training panty of the present invention.

Referring now to the Drawings, wherein like reference numerals designate like or corresponding parts throughout the views, FIG. 1 shows a perspective representation of the training panty of the present invention. The training panty 10 includes a pair of pants 12 having a front panel 14 and a rear panel 16. Pants 12 also include a waistband 20a, 20b and a pair of identical leg portions 22. Waistband 20a, 20b is a conventional elastic waistband formed as a partial waistband on each of panels 14 and 16 and is preferably provided at the top of panels 14 and 16. Leg portions 22 are similarly partially defined on each of panels 14 and 16.

Pants 12 are suitably constructed of "cloth", i.e., any flexible material, and are preferably of woven cotton, but may be of any other fabric suitable for underclothing. In the preferred embodiment, pants 12 are washable and long lasting.

Pants 12 are designed to fit snugly about the child's waist and to gather below the waist so that the child can move comfortably and can easily remove and replace the panty as necessary to perform bodily function. Leg portions 22 are designed to fit snugly about the child's leg to prevent leaking or egress of excreta toward the child's outer clothing and may include elastic along the area of leg portions 22 to adjust to the size of the child's leg and thus ensure a snug fit between the panty and the child's leg.

Figure 2:
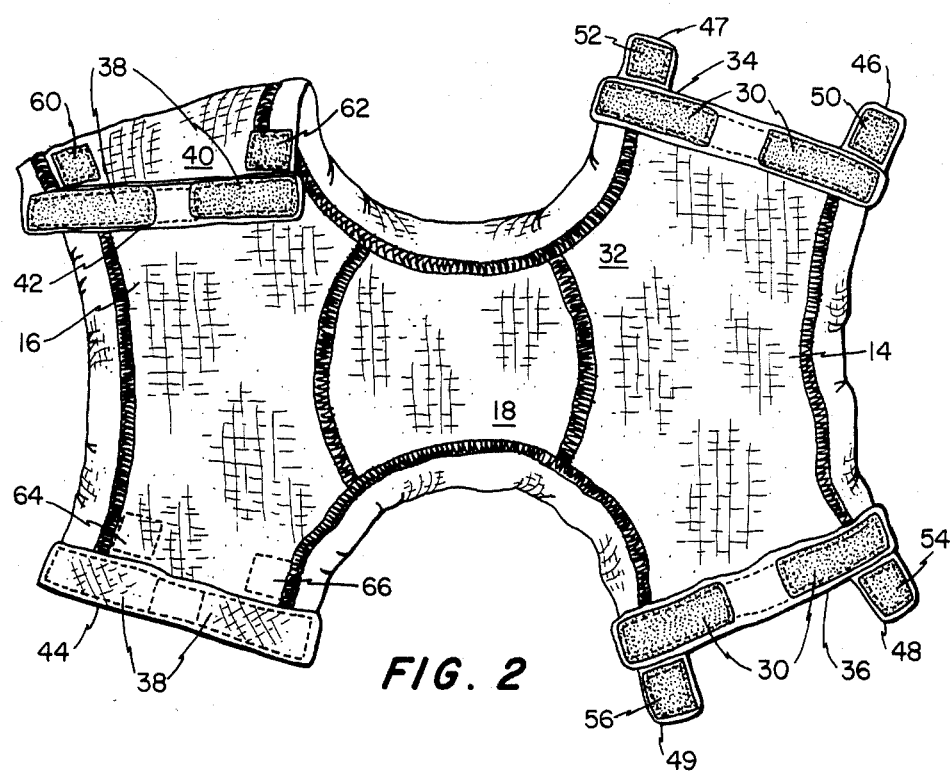
FIG. 2 is a plan view of the training panty of FIG. 1, showing the front and rear panels.

As best seen in FIG. 2, front panel 14 and rear panel 16 are substantially rectangular and are integrally joined at a crotch 18. Each of panels 14 and 16 has an inwardly facing (inside) surface and an outwardly facing (outside) surface and two opposing side edges. As seen in FIG. 2, a series of releasable contact fastening members 30 are positioned in closely spaced relation on the inside surface 32 of front panel 14 along each of its side edges 34, 36. A corresponding series of releasable contact fastening members 38 are positioned in closely spaced relation on the outside surface 40 of rear panel 16 along side edges 42, 44. Contact fastening members 38 are adapted to coact with contact fastening members 30 to releasably secure front panel 14 to rear panel 16. When secured together, panels 14 and 16 define waistband 20 and leg portions 22 to complete the training panty. In practice, this use of releasable contact fastening members is especially advantageous as it permits a mother to very easily and quickly remove the training panty to expose the child's body by simply pulling apart contact fastening members 30 and 38 to thus separate the front and rear panels.

An important aspect of the present invention is the design of pants 12 to gather below the child's waist. This gather as described above permits the child to move comfortably and also prevents inadvertent unfastening of the training panty. To further ensure that the panty is comfortable and resists inadvertent unfastening, in the preferred embodiment shown in FIG. 2, contact fastening members 30 and 38 are configured as a plurality (in FIG. 2, two) of discrete contact fastening elements aligned along the side edges of the opposing surfaces of panels 14 and 16 in spaced relation. Thus when the panels are secured together, this tandem line of fastening elements will produce a closure which contains gaps. This is in contrast to a substantially continuous closure that would be created by the use of a single fastening element extending along the entire length of the side edges. One such gap would be produced at area 13 (FIG. 1) between adjacent fastening members when the panty is worn.

In the preferred embodiment, ear flaps are provided at the topmost and lowermost portions of front panel 14 at the side edges thereof to facilitate separation of the front and rear panels. As shown in FIG. 2, a first pair of identical ear flaps 46 and 47 are provided on side 34 of front panel 14. Ear flaps 46 and 47 extend laterally from side 34 with ear flap 46 extending outwardly from side 34 at a point proximate the top end of front panel 14 and ear flap 47 extending outwardly from side 34 at a point proximate the bottom end of front panel 14. A substantially identical pair of laterally extending ear flaps 48, 49 are provided on opposing side 36 of front panel 14 and extend from side 36 at points proximate the top and bottom ends of front panel 14. Releasable contact fastening members 50, 52, 54, and 56 are provided on the inside surfaces of ear flaps 46, 47, 48, and 49, respectively, and are adapted to coact respectively with contact fastening members 60, 62, 64 and 66 positioned on the outside surface of rear panel 16.

Contact fastening members 30, 50, 52, 54 and 56 and 38, 60, 62, 64 and 66 may be of various materials, for example material sold under the trademark "VELCRO", with fasteners 30, 50, 52, 54 and 56 comprising loop-type fasteners and fasteners 38, 60, 62, 64 and 66 comprising complimentary hook-type fasteners.

In an alternative embodiment, not shown, decorative items, e.g. lace or buttons, may be arranged on the outside surface of front panel 14 overlaying side edges 34, 36 to thereby enhance the attractiveness of the training panty.

Figure 3:
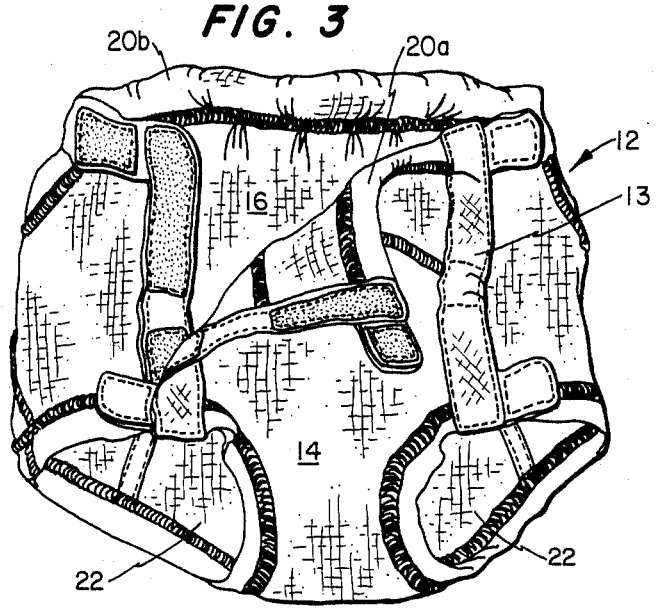
FIG. 3 illustrates an alternative embodiment of the training panty of FIG. 1.
Figure 4:
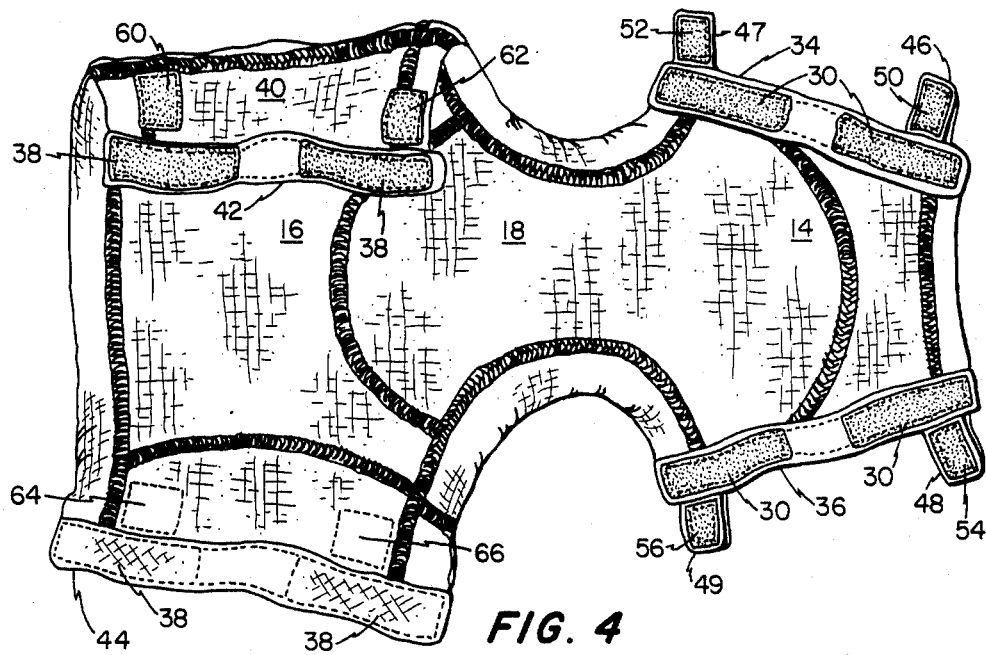
FIG. 4 is a plan view of the training panty of FIG. 3, showing the front and rear panels.

In FIG. 3, an alternative embodiment is shown in which front panel 14 is constructed to overlay the front midsection only of the body of the child wearer. As shown in FIG. 3, rear panel 16 is constructed to partially encircle the child's body and to be removably secured to front panel 14 at a location proximate the front midsection of the child's body. At best seen in FIG. 4, front panel 14 is here substantially smaller than rear panel 16. This is in contrast to the embodiment shown in FIGS. 1 and 2 wherein the panels are substantially identical in size. This construction is suitable used for larger children as it provides substantial gather proximate the child's midsection.

In summary, a training panty has been disclosed which is simple in construction and which is easily removed and replaced by the child when necessary to perform natural bodily functions. The training panty includes a pair of pants having a front and rear portion integrally joined together at a crotch and defining a waistband and a pair of identical leg portions. Releasable contact fastening means are provided on the front and rear panels to facilitate removal of the garment when it becomes soiled and to provide easy access to the child's body for cleaning.

Although the preferred embodiment has been described in detail, it should be understood that various changes, substitutions and alterations can be made therein without departing from the spirit and scope of the invention as defined by the appended claims.

What is claimed is:

1. A training panty for young children comprising a panty body having a front panel and a rear integrally joined together at a crotch and dimensioned to form leg openings when worn;

said front panel having opposed sides and having a partial elastic waistband formed at its upper edge;

said front panel further including contact fastening means positioned on its inside surface along each of said sides;

said rear panel having opposed sides and having a partial elastic waistband formed at its upper edge;

said rear panel further including contact fastening means positioned on its outside surface along each of said sides adapted to correspond symmetrically to the contact fastening means of said front panel so that said rear panel may be releasably secured to said front panel to define an elastic waistband and a pair of identical leg openings, said elastic waistband allowing the panty to be easily removed and replaced by a child wearer;

said contact fastening means disposed on said front panel and said rear panel comprise a plurality of discrete contact fastening members disposed in spaced relation along said opposing sides of each of said front and rear panels so that when said front panel is secured to said rear panel a closure is produced which contains gaps between adjacent ones of said fastening members to thus prevent inadvertently unfastening of the front and rear panels, said contact fastening members comprising loop-type fasteners positioned on the inside surface of said front panel and hook-type fasteners attached to the outside surface of said rear panel and adapted to coact with said loop-type fasteners to releasably secure said front panel to said rear panel;

a first pair of flaps extending laterally from a first side of said front panel, one of said flaps extending outwardly from said front panel from a point proximate the upper edge of said front panel from a point proximate the upper edge of said front panel and the other flap extending outwardly from said front panel from a point proximate the lower edge of said front panel, each of said flaps having a contact fastening member positioned on the inside surface thereof;

a second pair of flaps extending laterally from the opposing side of said front panel, one of said flaps extending outwardly from said front panel from a point proximate the upper edge of said front panel and the other flap extending outwardly from said front panel from a point proximate the lower edge of said front panel, each of said flaps having a contact fastening member positioned on the inside surface thereof;

a first pair of laterally extending contact fastening members positioned on the outside surface of said rear panel on a first side thereof and adapted to co-act with the contact fastening members on said first pair of flaps on said front panel so that said flaps can be removably secured to said rear panel on said first side thereof; and a second pair of laterally extending contact fastening members positioned on the outside surface of said rear panel on the opposing side thereof and adapted to co-act with the contact fastening members on said second pair of flaps on said front panel so that said flaps can be removably secured to said rear panel on said opposing side thereof.

2. The training panty of claim 3 wherein decorative elements are arranged on the outside surface of said front panel overlaying said contact fastening means positioned on the inside surface thereof to thereby enhance the attractiveness of the training panty.

3. The training panty of claim 2 wherein said decorative elements comprise lace or buttons.

4. The training panty of claim 1 wherein elastic is sewn into the panty along the area of said leg openings to allow the leg openings to automatically adjust to the size of the child's leg to provide a snug fit between the panty and the child's leg.

5. The training panty of claim 1 wherein said panty body is constructed of cotton.

6. The training panty of claim 1 wherein said front panel is substantially smaller than said rear panel and is constructed to overlay the front midsection only of the body of the child wearer and wherein said rear panel is constructed to partially encircle the child's body and to be releasably secured to said front panel at a location proximate the front midsection of the child's body.

* * * * *